United States Patent [19]

Pohmer et al.

[11] Patent Number: 5,502,251

[45] Date of Patent: Mar. 26, 1996

[54] IMIDES AND THEIR SALTS, AS WELL AS THEIR USE

[75] Inventors: Klaus Pohmer, Cologne; Rainer Weber, Odenthal; Cornelia Dörzbach-Lange, Kuerten-Bechen; Karlheinz Stachulla; Hans-Heinrich Moretto, both of Leverkusen; Manfred Wienand, Bergisch Gladbach, all of Germany

[73] Assignee: Bayer AG, Leverkusen, Germany

[21] Appl. No.: 383,702

[22] Filed: Feb. 1, 1995

Related U.S. Application Data

[63] Continuation of Ser. No. 60,995, May 14, 1993, abandoned.

[30] Foreign Application Priority Data

May 26, 1992 [DE] Germany ............... 42 17 366.3

[51] Int. Cl.$^6$ ............. C07C 311/15; C07C 311/09; C07C 311/03; C07C 233/31
[52] U.S. Cl. ............. 564/82; 564/98; 564/99; 564/155; 564/159
[58] Field of Search .............. 564/74, 82, 98, 564/99, 155, 159

[56] References Cited

U.S. PATENT DOCUMENTS

| | | | |
|---|---|---|---|
| 2,292,997 | 8/1942 | Hentrich et al. | 260/556 |
| 3,041,374 | 6/1962 | Gregory | 260/556 |
| 3,637,845 | 1/1972 | Moore et al. | 260/556 F |
| 3,661,990 | 5/1972 | Harrington | 564/82 |
| 3,705,185 | 12/1972 | Moore et al. | 260/465 D |
| 4,266,078 | 5/1981 | Pallos | 564/91 |
| 4,307,170 | 12/1981 | Desjarlais | 430/147 |

FOREIGN PATENT DOCUMENTS

| | | | |
|---|---|---|---|
| 2239817 | 2/1974 | Germany . | |
| 1142187 | 4/1967 | United Kingdom | 564/79 |

OTHER PUBLICATIONS

Chemical Abstracts Chemical Substance Index 11th Collective Index Columbus, Ohio, US p. 5365.
Chemical Abstracts Chemical Substance Index 11th Collective Index Columbus, Ohio, US p. 5423.
Chemical Abstracts Chemical Substance Index 12th Collective Index Columbus, Ohio, US p. 7542.
Journal Of Organic Chemistry Bd. 50, 1985, Washington, D.C., US pp. 4993–4996 H Nagasawa et al * p. 4996, Line 34*.
Chemical Abstracts, vol. 82, 1975, Columbus Ohio, US; abstract No. 30924, p. 467; Column 1; * Zusammenfassung * & IZV.AKAD.NAUK SSSR,SER.KHIM Nr. 10, 1974, pp.2272–2275.
Chemical Abstracts, vol. 113, 1990, Columbus, Ohio, US; abstract No. 172209, p. 722; col. 1; * Zusammenfassung * & ZH.OBSHCH.KHIM. Bd. 60, Nr. 5, 1990, pp. 1187–1189.
J. N. Meussdoerffer and H. Niederprüm, "Fluortenside unde fluorhaltige Phobiermittel–grenzflächenaktive Perfluorverbindungen", *Chemikerzeitung* 104, (1980) 45–52).

*Primary Examiner*—Peter O'Sullivan
*Attorney, Agent, or Firm*—Connolly & Hutz

[57] ABSTRACT

Fluoroalkyl- and fluoroaryl-group-containing imides and their salts of general formula (I)

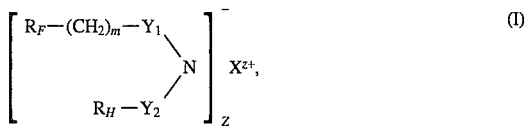

wherein $R_F$ is a fluoroalkyl group with 1 to 18 carbon atoms, a fluoroaryl group with 6 to 12 carbon atoms or a mixed fluoroalkylaryl group with 7 to 18 carbon atoms, wherein the carbon chain can also be interrupted by oxygen atoms, $R_H$ is an alkyl group with 1 to 30 carbon atoms, an aryl group with 6 to 12 carbon atoms or a mixed alkylaryl group with 7 to 30 carbon atoms, wherein the carbon chain of the group can also be interrupted by oxygen, nitrogen or sulphur atoms, $Y_1$ and $Y_2$ independently of each other represent a

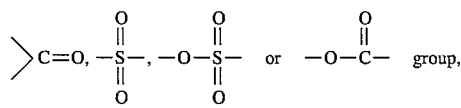

X is a hydrogen cation or a uni- or multivalent cation,
m is a whole number from 0 to 6, and
z is a whole number from 1 to 7 corresponding to the charge of the cation X.

9 Claims, 1 Drawing Sheet

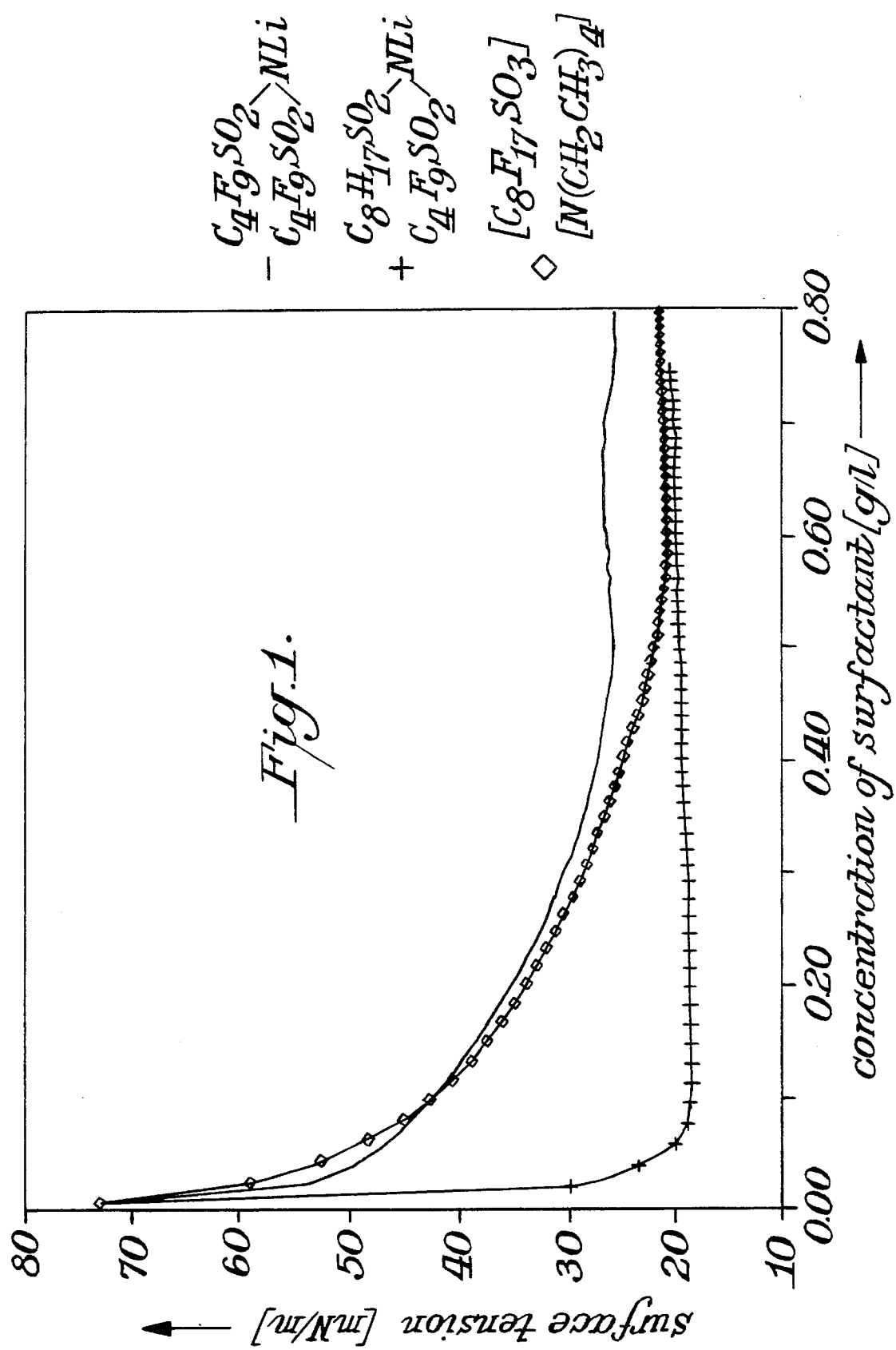

IMIDES AND THEIR SALTS, AS WELL AS THEIR USE

This application is a continuation of application Ser. No. 08/060,995 filed on May 14, 1993, which is now abandoned.

BACKGROUND OF THE INVENTION

1. Field of the Invention

The present invention relates to new imides and their salts as well as their use as surfactant agents.

2. Description of the Related Art

Owing to their high surface activity, chemical compounds containing perfluoroalkyl groups have numerous applications in technology. Typical applications are the suppression of sprays in electroplating, the improvement of levelling and wetting properties of lacquers, dispersion binders or floor maintenance agents, and the spreading of water on burning nonpolar liquids during the use of fire extinguishing agents that form a water film (cf. J. N. MeuBdoerffer and H. Niederprüm, Chemikerzeitung 104 (1980) 45–52). Examples of such compounds are:

[$C_8F_{17}SO_3$]K

[$C_7F_{15}COO$][Na]

[$C_8F_{17}SO_2N(C_2H_5)CH_2COO$]K

[$C_8F_{17}SO_3$][$N(CH_2CH_3)_4$].

Routes for the synthesis of the above compounds are likewise described in "J. N. MeuBdoerffer and H. Niederprüm, Chemikerzeitung 104 (1980) 45–52". Furthermore, according to DE-A 2 239 817, bis-perfluoroalkane-sulphonamides of the general formula $$R_FSO_2-\underset{X}{N}-SO_2RF$$

and their use as surfactants are known.

The perfluorinated starting compounds from which the aforementioned compounds are produced are themselves produced by three different synthetic routes:

a) electrochemical fluorination, b) telomerization of perfluoroolefins, especially tetrafluoroethylane c) oligomerization of tetrafluoroethylene.

Since the methods mentioned for producing the perfluorinated starting materials are technically very demanding, the resulting costs in the production of the desired chemical compounds containing perfluoroalkyl groups are high.

BRIEF DESCRIPTION OF THE DRAWING

FIG. 1 is a graphical representation of the effect of surfactant concentration on the surface tension of water to the compound of Example 27 and two known perfluoro surfactants.

DESCRIPTION OF THE INVENTION

It was the problem to make available more effective chemical compounds that can be used as surfactant agents and that are less expensive to produce.

This problem has been solved by the imides according to the invention and their salts.

A subject of the invention is fluoroalkyl- and fluoroaryl-group-containing imides and their salts of general formula (I).

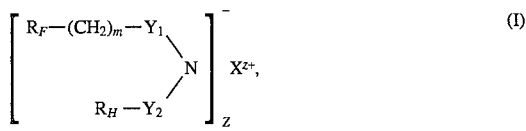

wherein $R_F$ is a fluoroalkyl group with 1 to 18 carbon atoms, a fluoroaryl group with 6 to 12 carbon atoms or a mixed fluoroalkylaryl group with 7 to 18 carbon atoms, wherein the carbon chain can also be interrupted by oxygen atoms, $R_H$ is an alkyl group with 1 to 30 carbon atoms, an aryl group with 6 to 12 carbon atoms or a mixed alkylaryl group with 7 to 30 carbon atoms, wherein the carbon chain of the group can also be interrupted by oxygen, nitrogen or sulphur atoms $Y_1$ and $Y_2$ independently of each other represent a

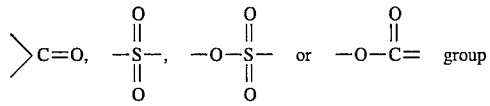

group

X is a hydrogen cation or a uni- or multivalent cation, m is a whole number from 0 to 6 and z is a whole number corresponding to the charge of the cation X.

The fluoroalkyl- and fluoroaryl-group-containing imides and their salts are preferably those in which $R_F$ is a fluoroalkyl group with 3 to 10 carbon atoms or a fluoroaryl group with 6 to 12 carbon atoms.

Fluoroalkyl- and fluoroaryl-group-containing imides and their salts are preferred in which $R_F$ represents a perfluoroalkyl group with 3 to 10 carbon atoms or a perfluoroaryl group with 6 to 12 carbon atoms.

Imides and their salts are especially preferred in which $R_H$ represents an alkyl group with 6 to 20 carbon atoms, an aryl group with 6 to 12 carbon atoms or a mixed alkylaryl group with 7 to 20 carbon atoms.

Imides and their salts are especially preferred in which $Y_1$ and $Y_2$ independently of each other represent a

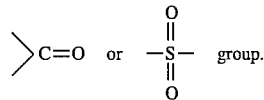

group.

Imides and their salts in which m is 0 are especially preferred.

Preferably used as the cation X are alkali or alkaline earth cations, ammonium cations or mono- or poly- alkyl- and/or aryl-substituted ammonium cations or polycations.

Especially preferred imides or imide salts have e.g. the following structures

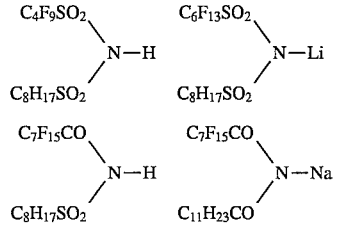

The imides according to the invention and their salts can be produced e.g. by multistage reaction of fluorosulphonic acids, fluorocarboxylic acids or their derivatives with ammonia and sulphonic acids, carboxylic acids or their derivatives. A possible synthetic route is given below by way of example.

In the first stage the salt of the fluorosulphonic or fluorocarboxylic acid amide is produced:

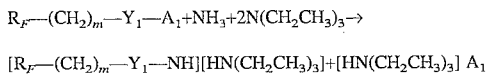

$[R_F—(CH_2)_m—Y_1—NH][HN(CH_2CH_3)_3]+[HN(CH_2CH_3)_3] A_1$ wherein $R_F$, $Y_1$ and m have the same meaning as above and $A_1$ is a reactive leaving group, as for example a halogen atom or a hydroxyl, alkoxyl or carboxyl group.

In the second stage the fluorosulphonic or fluorocarboxylic acid amide salt formed is converted to the triethylammonium salt of the imide:

$[R_F—(CH_2)_m—Y_1—NH][NH(CH_2CH_3)_3]$ +

$R_H—Y_2—A_2+N(CH_2CH_3)_3 \longrightarrow$

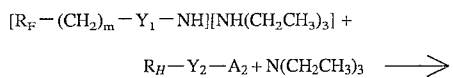

wherein $R_H$ and $Y_2$ have the same meaning as above and $A_2$ is a reactive leaving group, as e.g. a halogen atom or a hydroxyl, alkoxyl or carboxyl group.

In a third stage the triethylammonium salt can be reacted with sulphuric acid, as a result of which the free imide is formed:

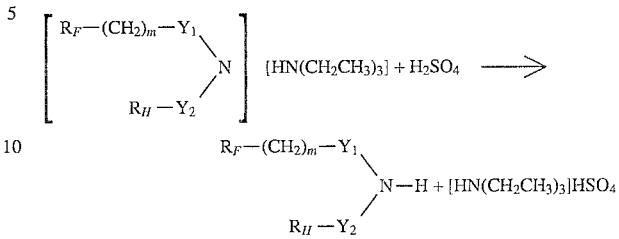

or converted with a base into any salt:

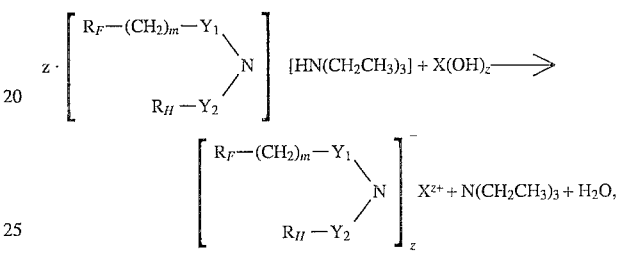

where X and z have the same meaning as above.

For the aforesaid multistage process, the following starting compounds can be used:

| Examples of fluorocarboxylic acids: | |
|---|---|
| Perfluoroheptanoic acid | $CF_3(CF_2)_5COOH$ |
| Perfluorooctanoic acid | $CF_3(CF_2)_6COOH$ |
| Perfluorononanoic acid | $CF_3(CF_2)_7COOH$ |
| Perfluoroether carboxylic acid dimer | $CF_3(CF_2)_2OCF(CF_3)COOH$ |
| Perfluoroether carboxylic acid trimer | $CF_3(CF_2)[CF_2OCF(CF_3)]_2COOH$ |
| Perfluoroether carboxylic acid tetramer | $CF_3(CF_2)[CF_2OCF(CF_3)]_3COOH$ |
| Perfluorobenzoic acid | $C_6F_5COOH$ |
| 2,2,3,3,4,4,5,5,6,6,7,7-dodecafluoroheptanoic acid | $H(CF_2)_6COOH$ |
| 4,4,5,5,6,6,7,7,8,8,9,9-tridecafluorononanoic acid | $CF_3(CF_2)_5(CH_2)_2COOH$ |
| 4,4,5,5,6,6,7,7,8,8,9,9,10,10,11,11,11-heptadecafluoroundecanoic acid | $CF_3(CF_2)_7(CH_2)_2COOH$ |
| 2-tetrafluoroethoxyacetic acid | $H(CF_2)_2OCH_2COOH$ |
| 2-hexafluoropropoxyacetic acid | $CF_3CHFCF_2OCH_2COOH$ |
| Examples of fluorosulphonic acids: | |
| Perfluorobutanesulphonic acid | $CF_3(CF_2)_3SO_3H$ |
| Perfluorohexanesulphonic acid | $CF_3(CF_2)_5SO_3H$ |
| Perfluorooctanesulphonic acid | $CF_3(CF_2)_7SO_3H$ |
| Perfluorobenzenesulphonic acid | $C_6F_5SO_3H$ |
| Perfluorotoluenesulphonic acid | $CF_3C_6F_4SO_3H$ |
| Examples of fluorosulphonic or fluorocarboxylic acid derivatives: | |
| Perfluorobutyric anhydride | $[CF_3(CF_2)_2CO]_2O$ |
| Perfluorobutyryl chloride | $CF_3(CF_2)_2COCl$ |
| Ethyl perfluorobutyrate | $CF_3(CF_2)_2COOC_2H_5$ |
| Perfluorobutanesulphonyl fluoride | $CF_3(CF_2)_3SO_2F$ |
| Perfluorohexanesulphonyl fluoride | $CF_3(CF_2)_5SO_2F$ |
| Perfluorooctanesulphonyl fluoride | $CF_3(CF_2)_7SO_2F$ |
| Perfluorobenzoyl chloride | $C_6F_5COCl$ |
| Perfluorobenzenesulphonyl chloride | $C_6F_5SO_2Cl$ |
| Examples of carboxylic acids: | |
| n-Butyric acid | $CH_3CH_2CH_2COOH$ |

| | -continued |
|---|---|
| n-Pentanoic acid | $CH_3(CH_2)_3COOH$ |
| n-Hexanoic acid | $CH_3(CH_2)_4COOH$ |
| n-Heptanoic acid | $CH_3(CH_2)_5COOH$ |
| n-Octanoic acid | $CH_3(CH_2)_6COOH$ |
| n-Nonanoic acid | $CH_3(CH_2)_7COOH$ |
| n-Decanoic acid | $CH_3(CH_2)_8COOH$ |
| n-Undecanoic acid | $CH_3(CH_2)_9COOH$ |
| n-Dodecanoic acid | $CH_3(CH_2)_{10}COOH$ |
| 2-Methylpropionic acid | $(CH_3)_2CHCOOH$ |
| 3-Methylbutyric acid | $(CH_3)_2CHCH_2COOH$ |
| 2,2-Dimethylpropionic acid | $(CH_3)_3CCOOH$ |
| 2-Methylbutyric acid | $CH_3CH_2CH(CH_3)_{COOH}$ |
| 2-Ethylbutyric acid | $CH_3CH_2CH(C_2H_5)COOH$ |
| 2-Ethylhexanoic acid | $CH_3(CH_2)_3CH(C_2H_5)COOH$ |
| Isomeric $C_8$-acids | $C_7H_{15}COOH$ |
| Isomeric $C_9$-acids | $C_8H_{17}COOH$ |
| Isomeric $C_{13}$-acids | $C_{12}H_{25}COOH$ |
| Nonadecanoic acid | $C_{18}H_{37}COOH$ |
| Cyclohexanecarboxylic acid | $C_6H_{11}COOH$ |
| Acrylic acid | $CH_2=CHCOOH$ |
| 2-Methacrylic acid | $CH_2=C(CH_3)COOH$ |
| trans-3-Methacrylic acid | $CH_3CH=CHCOOH$ |
| cis-3-Methacrylic acid | $CH_3CH=CHCOOH$ |
| 2,3-Dimethylacrylic acid | $CH_3CH=C(CH_3)COOH$ |
| 2,4-Hexadienoic acid | $CH_3CH=CHCH=CHCOOH$ |
| 11-Undecenoic acid | $CH_2=(CH_2)_8COOH$ |
| Propiolic acid | $CH\equiv CCOOH$ |
| Benzoic acid | $C_6H_5COOH$ |
| Toluic acid | $CH_3C_6H_4COOH$ |
| Phenylacetic acid | $C_6H_5CH_2COOH$ |
| Naphthylacetic acid | $CH_{10}H_7CH_2COOH$ |
| Examples of sulphonic acids: | |
| Methanesulphonic acid | $CH_3SO_3H$ |
| Ethanesulphonic acid | $CH_3CH_2SO_3H$ |
| Propanesulphonic acid | $CH_3(CH_2)_2SO_3H$ |
| Butanesulphonic acid | $CH_3(CH_2)_3SO_3H$ |
| Pentanesulphonic acid | $CH_3(CH_2)_4SO_3H$ |
| Hexanesulphonic acid | $CH_3(CH_2)_5SO_3H$ |
| Vinylsulphonic acid | $CH_2=CHSO_3H$ |
| Methallylsulphonic acid | $CH_2=C(CH_3)CH_2SO_3H$ |
| Benzenesulphonic acid | $C_6H_5SO_3H$ |
| Toluenesulphonic acid | $CH_3C_6H_4SO_3H$ |
| Examples of sulphonic acid or carboxylic acid derivatives: | |
| Sulphonyl/Carbonyl halides | |
| Sulphonic/Carboxylic acid esters | |
| Sulphonic/Carboxylic acid anhydrides | |
| Sulphonate/Carboxylate salts | |

In the imide salts according to the invention, X preferably represents a cation from the series of the alkali or alkaline earth cations, an ammonium cation or a mono- or polyalkyl-and/or -arylsubstituted ammonium cation. Examples of such cations are: $Na^+$, $Li^+$, $K^+$, $Ca^{2+}$, $Mg^{2+}$ and tetraethylammonium cation.

A further subject of the invention is the use of the imides according to the invention and their salts as surfactant agents.

On the basis of the very high surface activity of the imides and their salts according to the invention, which in some cases is higher than that of the known chemical compounds containing perfluoro groups, the imides and their salts according to the invention act as highly active surfactants, whose activity is developed more rapidly than that of the known compounds containing perfluoroalkyl groups, whereby they can be used for example in the following fields of application:

In electrolytic processes (e.g. in electroplating with chromium, copper and nickel, in anodizing and in electrolytic degreasing), the compounds according to the invention can be added to suppress spray and to prevent drag-out losses.

In non-electrolytic bath processes (e.g. in chemical copper plating or nickel plating, in chemical degreasing or derusting, in etching or engraving, in dip polishing, in pickling, black finishing or passivation, in anodizing or stripping), the compounds according to the invention can be added as spray suppressant and cleansing aid.

In cleansing and preserving agents (e.g. in cleansing agents for glass, stoves, cars, buildings, facades or metal surfaces, in stain removers, in shampoos, in polishes for furniture, cars etc., in self-polishing emulsions or in waxes), the compounds according to the invention can be added as levelling, spreading and wetting agents as well as to promote the properties that prevent re-soiling.

The compounds according to the invention can be used alone or in formulations as anti-condensation agents or tarnish preventives (e.g. for glasses, metals or plastics).

The compounds according to the invention can also be used alone or in formulations as corrosion inhibitors or anticorrosive coatings (e.g. in polymerization reactions, for fillers, fibres, salts or magnetic solids, in lacquers or in blood substitutes).

On the basis of their tendency to form gas-tight barrier layers and consequently to prevent the evaporation or volatilization of liquids, the compounds according to the invention are also suitable as additives to fire extinguishing agents.

The compounds according to the invention can be used as mould release agents.

In paints and lacquers an addition of the compounds according to the invention improves the levelling, wetting and adhesive properties. Also, by promoting deaeration they prevent the formation of surface defects (as e.g. cratering or edge receding). By their addition, furthermore, the distribution of the pigment is improved. Particularly advantageous is the foam destabilizing action of the compounds according to the invention in recipes for the production of water-dilutable lacquers.

The tendency of the compounds according to the invention to form hydrophobic and oleophobic barrier layers enables them to be added to building protective agents (e.g. for insulation against environmental influences).

The compounds according to the invention can be used as flow agents or slip additives (e.g. in mineral ores or mineral salts, in magnetic tapes or in building materials).

The compounds according to the invention are suitable as lubricants, cutting oil additives or hydraulic oils.

The compounds according to the invention can be used as drilling additives (e.g. increasing efficiency in oil drilling).

The compounds according to the invention can be used in photographic chemicals or in film manufacture (e.g. as a wetting agent or antistatic agent).

The compounds according to the invention can be used in plant protection agents (e.g. as wetting and dispersion agents).

An addition of the compounds according to the invention to finishing agents for textiles, leather or paper can for example promote the wetting or penetration of the finishing agent, lead to defoaming or support its hydrophilic/oleophilic action.

The compounds according to the invention can be used as fire retardant agents (e.g. in plastics).

The use of the compounds according to the invention as liquid crystals is also possible.

On the basis of their acidic strength, the use of the compounds according to the invention as catalysts (e.g. in saponification or sulphonation reactions or in polymerization reactions) is possible.

The invention will be explained in more detail with the aid of the following examples.

EXAMPLE 1

In a mechanically agitated glass flask at room temperature, 0.4 mol (119.6 g) perfluorobutylsulphonamide and 0.8 mol (80.8 g) triethylamine are reacted, the reaction being exothermic. The charge is heated to reflux, 0.4 mol (87.6 g) lauroyl chloride is added, and the mixture is then stirred for a further 1 hour. After cooling to ca. 50° C., the pH value is adjusted to 6 with 20% HCl.

After repeated washing with water, the product phase is dried at 60° C. and 24 mbar. The yield of triethylammonium N-undecylcarbonylperfluorobutylsulphonimide is 180 g (77% of theory).

EXAMPLE 2

In a mechanically agitated glass flask at room temperature, 0.10 mol (4.2 g) lithium hydroxide monohydrate dissolved in 30 g water are added to 0.10 mol (58.2 g) triethylammonium N-undecylcarbonylperfluorobutylsulphonimide. The mixture is subsequently heated to reflux.

After 1 hour's stirring, water and triethylamine are distilled off at 90° C. The product obtained is dried at 60° C. and 24 mbar. The yield of the lithium salt of N-undecylcarbonylperfluorobutylsulphonimide is 46.6 g (93% of theory).

EXAMPLE 3

In a mechanically agitated glass flask at room temperature, 0.1 mol (53.4 g) perfluorooctylsulphonamide and 0.2 mol (20.2 g) triethylamine are reacted, the reaction being exothermic. The charge is heated to reflux, 0.1 mol (21.9 g) lauroyl chloride are charged, and the mixture stirred for a further 1 h. After cooling to ca. 50° C., the pH value is adjusted to 6 with 20% HCl.

After repeated washing with water, the product phase is dried at 60° C. and 24 mbar. The yield of triethylammonium N-undecylcarbonylperfluorooctylsulphonimide is 68 g (87% of theory).

EXAMPLE 4

In a mechanically agitated glass flask at room temperature, 0.03 mol (1.26 g) lithium hydroxide monohydrate dissolved in 30 g water are added to 0.03 mol (23.5 g) triethylammonium N-undecylcarbonylperfluorooctylsulphonimide. The mixture is subsequently heated to reflux.

After 1 hour's stirring, water and triethylamine are distilled off at 90° C. The product obtained is dried at 60° C. and 24 mbar. The yield of the lithium salt of N-undecylcarbonylperfluorooctylsulphonimide is 20.6 g (100% of theory).

EXAMPLE 5

In a mechanically agitated glass flask at room temperature, 0.5 mol (200 g) triethylammonium perfluorobutylsulphonamide and 0.5 mol (50.5 g) triethylamine are reacted, the reaction being exothermic. The charge is heated to reflux, 0.5 mol (81.3 g) octanoyl chloride are charged, and the mixture stirred for a further 1 h. After cooling to ca. 50° C., the pH value is adjusted to 6 with 20% HCl.

After repeated washing with water, the isolated product phase is dried at 60° C. and 24 mbar. The yield of triethylammonium N-heptylcarbonylperfluorobutylsulphonimide is 222 g (84% of theory).

EXAMPLE 6

In a mechanically agitated glass flask at room temperature, 0.1 mol (4.2 g) lithium hydroxide monohydrate dissolved in 30 g water are added to 0.1 mol (52.6 g) triethylammonium N-heptylcarbonylperfluorobutylsulphonimide. The mixture is subsequently heated to reflux.

After 1 hour's stirring, water and triethylamine are distilled off at 90° C. The product obtained is dried at 60° C. and 24 mbar. The yield of the lithium salt of N-heptylcarbonylperfluorobutylsulphonimide is 43.2 g (100% of theory).

EXAMPLE 7

In a mechanically agitated glass flask at room temperature, 0.5 mol (300 g) triethylammoniumperfluorooctylsulphonamide and 0.5 mol (50.5 g) triethylamine are reacted, the reaction being exothermic. The charge is heated to reflux, 0.5 mol (81.3 g) octanoyl chloride are charged, and the mixture stirred for a further 1 h. After cooling to ca. 50°

C., the pH value is adjusted to 6 with 20% HCl.

After repeated washing with water, the isolated product phase is dried at 60° C. and 24 mbar. The yield of triethylammonium N-heptylcarbonylperfluorooctylsulphonimide is 323 g (89% of theory).

EXAMPLE 8

In a mechanically agitated glass flask at room temperature, 0.1 mol (4.2 g) lithium hydroxide monohydrate dissolved in 30 g water are added to 0.1 mol (72.6 g) triethylammonium N-heptylcarbonylperfluorooctylsulphonimide. The mixture is subsequently heated to reflux.

After 1 hour's stirring, water and triethylamine are distilled off at 90° C. The product obtained is dried at 60° C. and 24 mbar. The yield of the lithium salt of N-heptylcarbonylperfluorooctylsulphonimide is 56.4 g (89% of theory).

EXAMPLE 9

In a mechanically agitated glass flask at room temperature, 0.5 mol (200 g) triethylammoniumperfluorobutylsulphonamide and 0.5 mol (50.5 g) triethylamine are reacted, the reaction being exothermic. The charge is heated to reflux, 0.5 mol (88.35 g) pelargonoyl chloride are charged, and the mixture stirred for a further 1 h. After cooling to ca. 50° C., the pH value is adjusted to 6 with 20% HCl.

After repeated washing with water, the isolated product phase is dried at 60° C. and 24 mbar. The yield of triethylammonium N-octylcarbonylperfluorobutylsulphonimide is 218 g (81% of theory).

EXAMPLE 10

In a mechanically agitated glass flask at room temperature, 0.1 mol (4.2 g) lithium hydroxide monohydrate dissolved in 30 g water are added to 0.1 mol (54 g) triethylammonium N-octylcarbonylperfluorobutylsulphonimide. The mixture is subsequently heated to reflux.

After 1 hour's stirring, water and triethylamine are distilled off at 90° C. The product obtained is dried at 60° C. and 24 mbar. The yield of the lithium salt of N-octylcarbonylperfluorobutylsulphonimide is 45.6 g (100% of theory).

EXAMPLE 11

In a mechanically agitated glass flask at room temperature, 0.30 mol (63.9 g) perfluoropropylcarboxamide and 0.60 mol (60.6 g) triethylamine are reacted, the reaction being exothermic. The charge is heated to reflux, 0.30 mol (44.6 g) heptanoyl chloride are charged, and the mixture stirred for a further 1 h. After cooling to ca. 50° C., the pH value is adjusted to 6 with 20% HCl.

After repeated washing with water, the isolated product phase is dried at 60° C. and 24 mbar. The yield of triethylammonium N-hexylcarbonylperfluoropropylcarboximide is 89.7 g (70% of theory).

EXAMPLE 12

In a mechanically agitated glass flask at room temperature, 0.15 mol (6.12 g) lithium hydroxide monohydrate dissolved in 30 g water are added to 0.15 mol (62.5 g) triethylammonium N-hexylcarbonylperfluoropropylcarboximide. The mixture is subsequently heated to reflux.

After 1 hour's stirring, water and triethylamine are distilled off at 90° C. The product obtained is dried at 60° C. and 24 mbar. The yield of the lithium salt of N-hexylcarbonylperfluoropropylcarboximide is 56.6 g (100% of theory).

EXAMPLE 13

In a mechanically agitated glass flask at room temperature, 0.30 mol (63.9 g) perfluoropropylcarboxamide and 0.60 mol (60.6 g) triethylamine are reacted, the reaction being exothermic. The charge is heated to reflux, 0.30 mol (48.0 g) octanoyl chloride are charged, and the mixture stirred for a further 1 h. After cooling to ca. 50° C., the pH value is adjusted to 6 with 20% HCl.

After repeated washing with water, the isolated product phase is dried at 60° C. and 24 mbar. The yield of triethylammonium N-heptylcarbonylperfluoropropylcarboximide is 102 g (77.1% of theory).

EXAMPLE 14

In a mechanically agitated glass flask at room temperature, 0.20 mol (8.5 g) lithium hydroxide monohydrate dissolved in 30 g water are added to 0.20 mol (89 g) triethylammonium N-heptylcarbonylperfluoropropylcarboximide. The mixture is subsequently heated to reflux.

After 1 hour's stirring, water and triethylamine are distilled off at 90° C. The product obtained is dried at 60° C. and 24 mbar. The yield of the lithium salt of N-heptylcarbonylperfluoropropylcarboximide is 70 g (100% of theory)

EXAMPLE 15

In a mechanically agitated glass flask at room temperature, 0.50 mol (56.5 g) trifluoroacetamide and 1.0 mol (101 g) triethylamine are reacted, the reaction being exothermic. The charge is heated to reflux, 0.5 mol (81.35 g) octanoyl chloride are charged, and the mixture stirred for a further 1 h. After cooling to ca. 50° C., the pH value is adjusted to 6 with 20% HCl.

After repeated washing with water, the isolated product phase is dried at 60° C. and 24 mbar. The yield of triethylammonium N-heptylcarbonyltrifluoromethylcarboximide is 66.2 g (36.6% of theory).

EXAMPLE 16

In a mechanically agitated glass flask at room temperature, 0.50 mol (56.5 g) trifluoroacetamide and 1.0 mol (101 g) triethylamine are reacted, the reaction being exothermic. The charge is heated to reflux, 0.5 mol (106.3 g) octylsulphonyl chloride are charged, and the mixture stirred for a further 1 h. After cooling to ca. 50° C., the pH value is adjusted to 6 with 20% HCl.

After repeated washing with water, the isolated product phase is dried at 60° C. and 24 mbar. The yield of triethylammonium N-octylsulphonyltrifluoromethylcarboximide is 195 g (100% of theory).

EXAMPLE 17

In a mechanically agitated glass flask at room temperature, 0.4 mol (85.2 g) heptafluorobutyramide and 0.8 mol (80.8 g) triethylamine are reacted, the reaction being exothermic. The charge is heated to reflux, 0.4 mol (78.4 g) octylsulphonyl fluoride are charged, and the mixture stirred for a further 1 h. After cooling to ca. 50° C., the pH value is adjusted to 6 with 20% HCl.

After repeated washing with hot water, the isolated product phase is dried at 60° C. and 24 mbar. The yield of triethylammonium N-octylsulphonylperfluoropropylcarboximide is 169 g (86% of theory).

EXAMPLE 18

In a mechanically agitated glass flask at room temperature, 0.25 mol (10.5 g) lithium hydroxide monohydrate dissolved in 30 g water are added to 0.25 mol (122.5 g) triethylammonium N-octylsulphonylperfluoropropylcarboximide. The mixture is subsequently heated to reflux.

After 1 hour's stirring, water and triethylamine are distilled off at 90° C. The product obtained is dried at 60° C. and 24 mbar. The yield of the lithium salt of N-octylsulphonylperfluoropropylcarboximide is 99.5 g (100% of theory).

EXAMPLE 19

In a mechanically agitated glass flask at room temperature, 0.20 mol (120 g) triethylammoniumperfluorooctylsulphonamide and 0.20 mol (20.2 g) triethylamine are reacted, the reaction being exothermic. The charge is heated to reflux, 0.2 mol (39.2 g) octylsulphonyl fluoride are charged, and the mixture stirred for a further 1 h. After cooling to ca. 50° C., the pH value is adjusted to 6 with 20% HCl.

After repeated washing with water, the isolated product phase is dried at 60° C. and 24 mbar. The yield of triethylammonium N-octylsulphonylperfluorooctylsulphonimide is 129 g (83% of theory).

EXAMPLE 20

In a mechanically agitated glass flask at room temperature, 0.1 mol (4.2 g) lithium hydroxide monohydrate dissolved in 30 g water are added to 0.1 mol (77.6 g) triethylammonium N-octylsulphonylperfluorooctylsulphonimide. The mixture is subsequently heated to reflux.

After 1 hour's stirring, water and triethylamine are distilled off at 90° C. The product obtained is dried at 60° C. and 24 mbar. The yield of the lithium salt of N-octylsulphonylperfluorooctylsulphonimide is 67.5 g (100% of theory).

EXAMPLE 21

In a mechanically agitated glass flask at room temperature, 0.1 mol (60 g) triethylammonium perfluorooctylsulphonamide and 0.1 mol (10 g) triethylamine in 150 ml diisopropyl ether are reacted, the reaction being exothermic. The charge is heated to reflux, 0.1 mol (19.1 g) tosyl chloride are charged, and the mixture stirred for a further 1 h. After cooling to ca. 50° C., the pH value is adjusted to 6 with 20% HCl.

The ether phase is washed repeatedly with water. Subsequently the ether is distilled off at 20° C. and 24 mbar. The yield of triethylammonium N-tosylperfluorooctylsulphonimide is 20 g (26.5% of theory).

EXAMPLE 22

In a mechanically agitated glass flask at room temperature, 0.1 mol (40 g) triethylammonium perfluorobutylsulphonamide and 0.1 mol (10 g) triethylamine in 150 ml diisopropyl ether are reacted, the reaction being exothermic. The charge is heated to reflux, 0.1 mol (19.1 g) tosyl chloride are charged, and the mixture stirred for a further 1 h. After cooling to ca. 50° C., the pH value is adjusted to 6 with 20% HCl.

The ether phase is washed repeatedly with water. Subsequently the ether is distilled off at 60° C. and 24 mbar. The yield of triethylammonium N-tosylperfluorobutylsulphonimide is 20 g (36.1% of theory).

EXAMPLE 23

In a mechanically agitated glass flask at room temperature, 0.25 mol (100 g) triethylammonium perfluorobutylsulphonamide and 0.25 mol (25 g) triethylamine are reacted, the reaction being exothermic. The charge is heated to reflux, 0.25 mol (49 g) octylsulphonyl fluoride are charged, and the mixture stirred for a further 1 h. After cooling to ca. 50° C., the pH value is adjusted to 6 with 20% HCl.

After repeated washing with water the product phase is dried at 60° C. and 24 mbar. The yield of triethylammonium N-octylsulphonylperfluorobutylsulphonimide is 135.9 g (94.4% of theory).

EXAMPLE 24

In a mechanically agitated glass flask at room temperature, 0.236 mol (9.4 g) sodium hydroxide dissolved in 60 g water are added to 0.236 mol (135.9 g) triethylammonium N-octylsulphonylperfluorobutylsulphonimide. The mixture is subsequently heated to reflux. After 1 hour's stirring, water and triethylamine are distilled off at 90° C. The product obtained is dried at 60° C. and 24 mbar. The yield of the sodium salt of N-octylsulphonylperfluorobutylsulphonimide is 17.3 g (100% of theory).

EXAMPLE 25

In a mechanically agitated glass flask at room temperature, 0.236 mol (13.2 g) potassium hydroxide mixed with 60 g water are added to 0.236 mol (135.9 g) triethylammonium N-octylsulphonylperfluorobutylsulphonimide. The mixture is subsequently heated to reflux. After 1 hour's stirring, water and triethylamine are distilled off at 90° C. The product obtained is dried at 60° C. and 24 mbar. The yield of the potassium salt of N-octylsulphonylperfluorobutylsulphonimide is 121.0 g (100% of theory).

EXAMPLE 26

In a mechanically agitated glass flask at room temperature, 0.236 mol (9.9 g) lithium hydroxide monohydrate dissolved in 60 g water are added to 0.236 mol (135.9 g) triethylammonium N-octylsulphonylperfluorobutylsulphonimide. The mixture is subsequently heated to reflux. After 1 hour's stirring, water and triethylamine are distilled off at 90° C. The product obtained is dried at 60° C. and 24 mbar. The yield of the lithium salt of N-octylsulphonylperfluorobutylsulphonimide is 113.5 g (100% of theory).

EXAMPLE 27

In this example the effectiveness as surfactant of lithium N-octylsulphonylperfluorobutylsulphonimide according to the invention is examined by comparison with two known perfluoro surfactants (lithium bis(perfluorobutyl)sulphonimide and tetraethylammonium perfluorooctylsulphonate). To this end the surface tension is measured with a tensiometer (Type TE 1C of the Lauda company) as a function of the surfactant concentration in water at 20° C. The results are shown in FIG. 1.

According to FIG. 1 a surface tension of ca. 20 mN/m is already reached with the compound of the invention at a clearly lower applied concentration than in the case of the known compounds.

What is claimed is:

1. Fluoroalkyl- and fluoroaryl-group-containing imides and their salts of general formula (I)

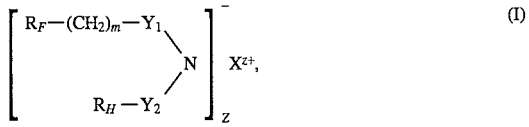  (I)

wherein $R_F$ is a perfluoroalkyl group with 3 to 10 carbon atoms or a perfluoroaryl group with 6 to 12 carbon atoms, $R_H$ is an alkyl group with 1 to 30 carbon atoms, an aryl group with 6 to 12 carbon atoms or a mixed alkylaryl group with 7 to 30 carbon atoms, $Y_1$ and $Y_2$ each represent a

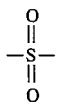

group,

X is a hydrogen cation or a uni- or multivalent cation, m is a whole number from 0 to 6, and z is a whole number from 1 to 7 corresponding to the charge of the cation X.

2. Imides and their salts according to claim 1, wherein $R_H$ is an alkyl group with 6 to 20 carbon atoms, an aryl group with 6 to 12 carbon atoms or a mixed alkylaryl group with 7 to 20 carbon atoms.

3. Imides and their salts according to claim 1, wherein m is 0.

4. Imides and their salts according to claim 1, wherein m is 0.

5. Imides and their salts according to claim 2, wherein m is 0.

6. Imide salts according to claim 1, wherein X is a cation selected from the alkali cations, the alkaline earth cations, an ammonium cation, a monoalkyl-substituted ammonium cation, a polyalkyl-substituted ammonium cation, a monoaryl-substituted ammonium cation, a polyaryl-substituted ammonium cation, a monoalkyl and monoaryl-substituted ammonium cation and a polyalkyl and polyaryl-substituted ammonium cation.

7. Imide salts according to claim 2, wherein X is a cation selected from the alkali cations, the alkaline earth cations, an ammonium cation, a monoalkyl-substituted ammonium cation, a polyalkyl-substituted ammonium cation, a monoaryl-substituted ammonium cation, a polyaryl-substituted ammonium cation, a monoalkyl and monoaryl-substituted ammonium cation and a polyalkyl and polyaryl-substituted ammonium cation.

8. Imide salts according to claim 3, wherein X is a cation selected from the alkali earth cations, the alkaline earth cations, an ammonium cation, a monoalkyl-substituted ammonium cation, a polyalkyl-substituted ammonium cation, a monoaryl-substituted ammonium cation, a polyaryl-substituted ammonium cation, a monoalkyl and monoaryl-substituted ammonium cation and a polyalkyl and polyaryl-substituted ammonium cation.

9. Imide salts according to claim 4, wherein X is a cation selected from the alkali cations, the alkaline earth cations, an ammonium cation, a monoalkyl-substituted ammonium cation, a polyalkyl-substituted ammonium cation, a monoaryl-substituted ammonium cation, a polyaryl-substituted ammonium cation, a monoalkyl and monoaryl-substituted ammonium cation and a polyalkyl and polyaryl-substituted ammonium cation.

* * * * *

UNITED STATES PATENT AND TRADEMARK OFFICE
CERTIFICATE OF CORRECTION

PATENT NO. : 5,502,251
DATED : March 26, 1996
INVENTOR(S) : Pohmer et al.

It is certified that error appears in the above-indentified patent and that said Letters Patent is hereby corrected as shown below:

In Claim 8, (Column 14, line 22) the words "alkali earth cations" should be --alkali cations--.

Signed and Sealed this

Twenty-ninth Day of October 1996

Attest:

BRUCE LEHMAN

*Attesting Officer*    Commissioner of Patents and Trademarks